United States Patent [19]

Anno

[11] Patent Number: 4,651,002

[45] Date of Patent: Mar. 17, 1987

[54] RADIOGRAPHIC METHOD AND APPARATUS FOR REDUCING THE EFFECTS OF SCATTER IN THE IMAGE

[75] Inventor: Hidero Anno, Tokyo, Japan

[73] Assignee: Kabushiki Kaisha Toshiba, Kawasaki, Japan

[21] Appl. No.: 705,377

[22] Filed: Feb. 25, 1985

[30] Foreign Application Priority Data

Feb. 29, 1984 [JP]  Japan ................................. 59-36246

[51] Int. Cl.⁴ ............................................. G01T 1/161
[52] U.S. Cl. .............................. 250/336.1; 250/363 S; 250/393; 250/395; 250/358.1; 378/155
[58] Field of Search .................... 378/155, 154, 87, 62, 378/6, 7; 250/358.1, 370 G, 363 SD, 336.1, 338 R, 395, 505.1, 370 H, 393, 363 SR, 363 SH

[56] References Cited

U.S. PATENT DOCUMENTS

| | | | |
|---|---|---|---|
| 4,097,748 | 6/1978 | Monvoisin | 378/146 |
| 4,149,080 | 4/1979 | Schittenhelm | 378/7 |
| 4,433,427 | 2/1984 | Barnea | 378/146 |
| 4,465,540 | 8/1984 | Albert | 156/252 |

FOREIGN PATENT DOCUMENTS 2377642 11/1978 France ...................... 250/363 SR 5175318 6/1976 Japan .

Primary Examiner—Janice A. Howell
Assistant Examiner—Constantine Hannaher
Attorney, Agent, or Firm—Cushman, Darby & Cushman

[57] ABSTRACT

In a radiographic method, first and second collimator elements are arranged between a radiation source and an image converter. When an object is irradiated with radiation beams, the collimator elements can be switched between first and second states. In the first state, the collimator elements pass both some of the transmitted radiation beams which are not scattered by the object and transmitted therethrough and scattered radiation beams which are scattered by the object so that a first radiation image is obtained in the form of electrical signals based on the transmitted radiation beams and the scattered radiation beams. In the second state, the collimator elements pass only some of the scattered radiation beams scattered by the object so that a second radiation image is obtained in the form of electrical signals based on only the scattered radiation beams. The first and second radiation images are electrically processed to reproduce and display a two-dimensional transmitted image which is not influenced by spatial variation of radiation-transmittance for the collimator elements and by the scattered radiation beams.

34 Claims, 12 Drawing Figures

F I G. 6
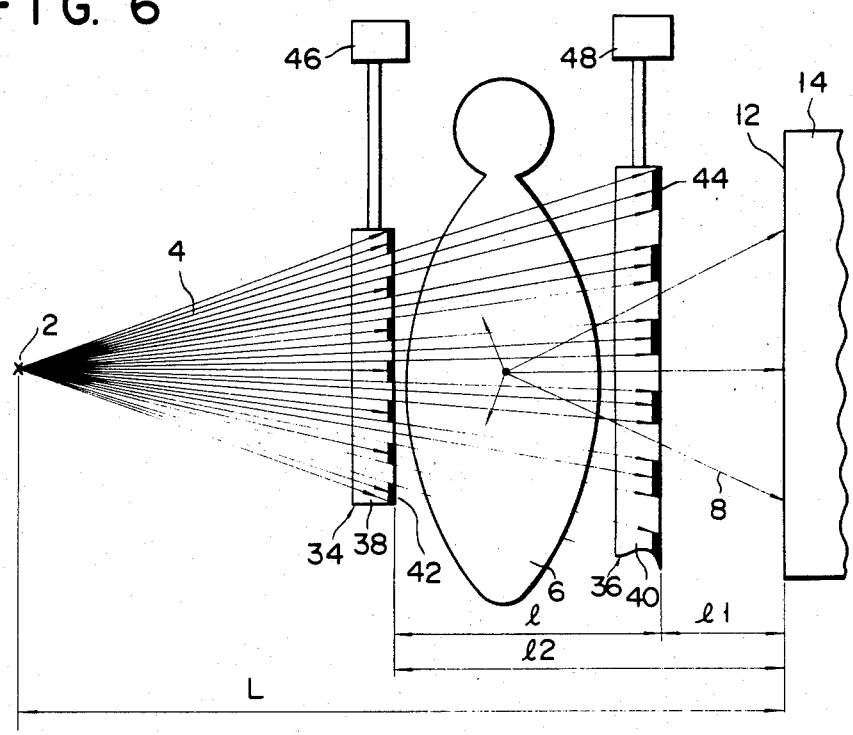
F I G. 7
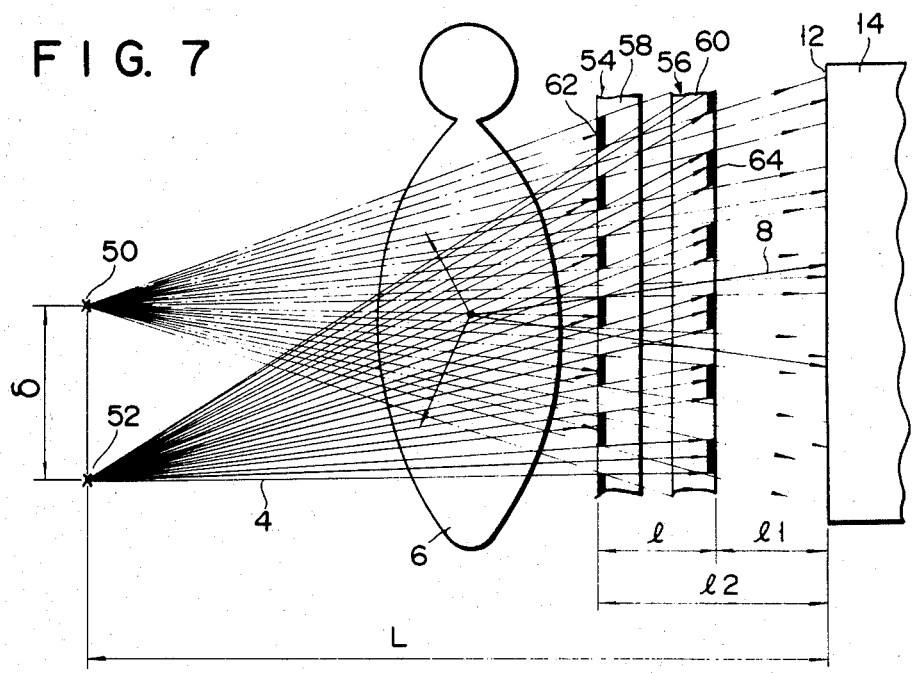

RADIOGRAPHIC METHOD AND APPARATUS FOR REDUCING THE EFFECTS OF SCATTER IN THE IMAGE

BACKGROUND OF THE INVENTION

The present invention relates to a radiographic method and apparatus for irradiating an object with a radiation beam and obtaining a two-dimensional transmitted image with the radiation beam transmitted through the object. Although the present invention is particularly effective and will be described with reference to X-ray radiography hereinafter, the present invention is not limited to X-ray radiography but is widely applicable to medical diagnosis or industrial inspection of structures using $\alpha$-, $\beta$- or $\gamma$-rays.

In X-ray radiography, when X-rays are transmitted through an object and reach a screen, they are considerably attenuated with respect to incident X-rays. X-rays incident on an object are considerably scattered at respective portions within the object and form scattered X-rays. For this reason, the transmitted X-ray image on the screen includes a scattered X-ray image component which largely lowers the contrast of the X-ray image. Various measures have been taken to eliminate scattered X-rays including, for example, the grid method, the Grädel method, and the slit scanning method. In the grid method, a grid is interposed between the object and the screen. Lead foil pieces are arranged in a stripe or matrix form in the grid. Scattered X-rays from the objects are attenuated by the grid. The attenuation factor of X-rays scattered from the object is larger than the attenuation factor of transmitted primary X-rays, so it is possible to improve the contrast of a transmitted X-ray image. However, if thin lead foil pieces are used, the eliminating effect on scattered X-rays is reduced as X-ray energy is increased. Furthermore, in such a case, the grid also produces some scattered X-rays. Because of these reasons, the improvement in the contrast of the transmitted X-ray image is limited.

According to the Grädel method, the screen is located at a position a maximum possible distance from the object. In this case, since the sources of scattered X-rays are respective portions of the object, the intensity of the scattered X-rays is attenuated in proportion to the second power of the inverse of the distance between the screen and the scattered X-ray sources, i.e., the object. However, transmitted primary X-rays on the screen are also attenuated in proportion to the second power of the inverse of the distance between the X-ray source and the screen. In this case, the output of the X-ray source, i.e., the X-ray tube must be increased. This means an increased X-ray dose on the object. In addition, when the distance between the object and the screen is excessively increased, blurred resolution will occur in a transmitted primary X-ray image depending upon the size of the X-ray focal point of the X-ray source.

In the slit scanning method, a slit is interposed between the X-ray source and the object and another slit is interposed between the object and the screen. X-rays from the X-ray source are limited by the slit between the X-ray source and the object to form a fan-shaped beam which scans the object. The slit between the object and the screen permits the transmission of the fan-shaped beam. These slits are synchronously scanned in one direction with respect to the object. Thus, only the transmitted primary X-rays which pass through the object reach the screen. In the slit scanning method, the contrast of the transmitted primary X-ray image is improved in comparison with that obtained by the grid or Grädel methods described above. However, in the slit scanning method, the time required for scanning the slits is lengthy, resulting in long radiographic imaging times. Therefore, if the object is in motion during this time, primary transmitted X-rays from a single position in the object are recorded at different positions on the screen and form a blurred transmitted X-ray image. Consequently, in the slit scanning method, the slits must be scanned at high speed. An apparatus adopting this method thus becomes complex in structure and bulky. The radiation time of X-rays is increased, and the electrical load on an X-ray tube (the X-ray source) is increased.

In order to resolve the problems with these methods, Japanese Patent Application No. 12071/1984 (original Dutch Application filed on Nov. 26, 1974) proposed an X-ray radiographic apparatus. In this X-ray radiographic apparatus, a plate is interposed between an X-ray source and an object. The plate has an X-ray transmittance which changes along a predetermined pattern so as to spatially modulate the intensity of primary X-rays reaching the object. Transmitted X-rays are supplied to an image intensifier. An output image from the image intensifier is converted into electrical signals which are subjected to analog signal processing by a video circuit.

According to the principle of this X-ray radiographic apparatus, the intensity of the primary X-rays incident on the subject is modulated so as to allow discrimination between components of the transmitted X-ray image attributable to the primary X-rays and the scattered X-rays. More specifically, when primary X-rays are spatially modulated by the plate, actual video signals are obtained as a sum of certain portions of the modulated signal and the non-modulated signal. Thus, only the modulated component in the video signal is utilized to reproduce a transmitted primary X-ray image which is not influenced by scattered X-rays.

In the X-ray radiography described above, the video circuit performs the analog image processing. A video signal modulated by a plate is used to generate a reference signal, and analog image processing is performed using this reference signal. However, precise image processing is generally impossible, resulting in unavoidable ripple components at wave portions corresponding to changes in modulation factor of the plate. Due to the presence of these ripple components, the displayed image includes a noise component which hinders medical diagnosis or industrial inspection of X-ray radiography.

SUMMARY OF THE INVENTION

It is an object of the present invention to provide a radiographic method and apparatus wherein conventional drawbacks are eliminated, adverse influences of scattered radiation from an object which results in degradation in contrast characteristics of a two-dimensional transmitted image of the object are eliminated, and a two-dimensional transmitted image of the object can be reproduced and displayed with an excellent contrast.

According to one radiographic method of the present invention, a radiation shielding means is arranged behind an object. When the object is irradiated with radiation beams, the radiation shielding means can be switched between first and second states. In the first state, the radiation shielding means passes both the transmitted primary radiation beams from the object and some scattered radiation beams scattered by the object. However, in the second state, the radiation shielding means shields the transmitted primary radiation beams and passes only the scattered radiation beams scattered by the object. When the object is irradiated with the radiation beams while the radiation shielding means is in the first state, a first radiation image of the object is obtained in the form of electrical signals based on the transmitted radiation beams transmitted through the object and the radiation shielding means and the scattered radiation beams scattered by the object and transmitted through the radiation shielding means. When the object is irradiated with the radiation beams while the radiation shielding means is in the second state, a second radiation image of the object is obtained in the form of electrical signals based only on the scattered radiation beams scattered by the object and transmitted through the radiation shielding means. The first and second radiation images are electrically processed, and an actual radiation image unaffected by the spatial modulation by the radiation shielding means and the scattered radiation beams is reproduced and displayed.

According to the method of the present invention, when the radiation shielding means is switched to the second state, the second radiation image is obtained based only on the scattered radiation beams. Thus, the second radiation image can be subtracted from the first radiation image which is influenced by both the transmitted and scattered radiation beams, after some intensity-correction of two images. For this reason, in this method, the influence of the scattered radiation beams can be eliminated, and a two-dimensional image of the object can be reproduced with excellent contrast characteristics.

In a radiographic apparatus according to the present invention, a radiation generating means irradiates an object with a conical radiation beam from a radiation source. A radiation shielding means is arranged in a radiation passing region between the radiation source and an image converter. When the radiation beam is irradiated, the radiation shielding means can be switched between first and second states. In the first state, the radiation shielding means passes both the primary radiation beams transmitted through the object and the radiation beams scattered by the object. However, in the second state, the radiation shielding means shields the transmitted primary radiation beams and passes some scattered radiation beams. The image converter is arranged behind the radiation shielding means as viewed from the radiation source. The image converter has a screen facing the object. When the radiation shielding means is in the first state, the image converter receives the first radiation image consisting of transmitted and scattered radiation beams on the screen and converts it into a visible image. When the radiation shielding means is in the second state, the image converter receives the second radiation image consisting of the main component of the scattered radiation beam on the screen and converts it into a visible image. An imaging device is arranged to correspond to the visible images of the image converter and electrically derives image data from the visible images corresponding to the first or second radiation image on the image converter screen. A reproducing/display means is electrically connected to the imaging device. The reproducing/display means stores the image data of first and second radiation images and electrically processes the image data to reproduce and display an actual radiographic image of an object from which the influence of scattered radiation beams is eliminated.

According to the radiographic apparatus of the present invention, when the radiation shielding means is switched to the second state, the second radiation image substantially consists only of the radiation beams scattered by the object. The reproducing/display means can equalize the second radiation image with the component of the first radiation image corresponding to the scattered radiation beam, and can subtract the equalized second radiation image from the first radiation image. Therefore, the radiographic apparatus of the present invention can reproduce and display a two-dimensional radiographic image of an object which has an excellent contrast and from which the influence of scattered radiation beams is removed.

BRIEF DESCRIPTION OF THE DRAWINGS

FIG. 6 is a schematic diagram similar to FIG. 3 illustrating a modification of the method of the present invention and illustrating X-rays emitted from an X-ray source when X-ray shielding elements different from those used in FIG. 1 are used in the X-ray radiographic apparatus shown in FIG. 1;

FIGS. 7 and 8 are schematic diagrams similar to FIGS. 3 and 6 illustrating X-ray radiation when two different X-ray focal points are used in the method according to the present invention;

DETAILED DESCRIPTION OF THE PREFERRED EMBODIMENTS

A first embodiment, in which a radiographic apparatus of the present invention is applied to an X-ray radiographic apparatus, will be described below with reference to FIGS. 1 to 5.

Figure 1:
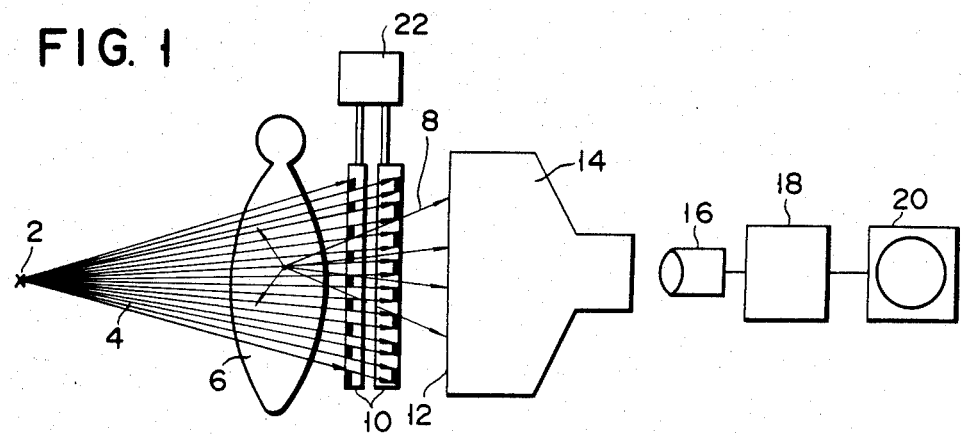
FIG. 1 is a schematic diagram illustrating an X-ray radiographic apparatus according to the present invention.

FIG. 1 shows the schematic construction of the X-ray radiographic apparatus. Referring to FIG. 1, an X-ray focal point 2 is shown at the left side. Primary X-rays 4 emitted from this X-ray source irradiate an object 6. The object 6 scatters secondary X-rays 8. First and second X-ray shielding elements 10, an X-ray image intensifier 14 with a screen 12, and a television camera 16 are sequentially arranged behind the object 6. The television camera 16 is electrically connected to a memory/operation device 18 which is, in turn, connected to a CRT 20. The memory/operation device 18 converts input video signals from the television camera 16 into digital signals and stores them. The digital signals are subjected to digital image processing, and a processed image is displayed on the CRT 20. A driver 22 is mounted above the pair of X-ray shielding elements 10. The driver 22 drives the elements 10 so as to insert one or both of the elements 10 between the object 6 and the image intensifier, to remove them, or to move or vibrate them.

Figure 2:
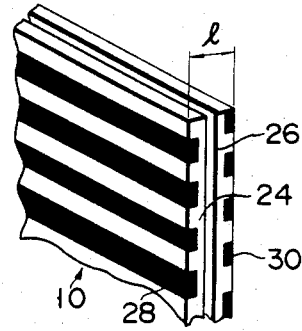
FIG. 2 is a partial enlarged perspective view of X-ray shielding elements shown in FIG. 1.

FIG. 2 schematically shows the structure of the elements 10. The elements 10 have opposing plates 24 and 26. The plate 24 has a number of first stripes 28 in the surface facing toward the object 6. The plate 26 has a number of second stripes 30 in the surface facing away from the object 6. The first and second stripes 28 and 30 consist of a substance having a high X-ray attentuation factor, e.g., lead. The plates 24 and 26 (as spacers) consist of a substance having a small X-ray attenuation factor, e.g., aluminium. The stripes 28 and 30 have a thickness such that the intensity of X-rays transmitted through the stripes 28 and 30 is negligible. When the stripes 28 and 30 consist of lead, for example, they have a thickness of about 0.1 to 1 mm.

Figure 3:
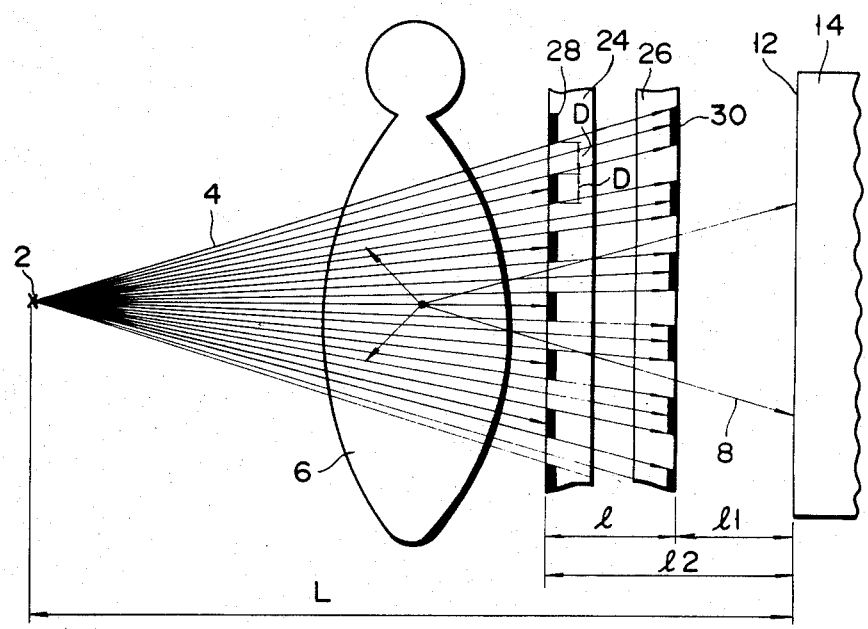
FIG. 3 is a schematic diagram showing X-rays emitted from an X-ray source when the X-ray shielding elements shown in FIG. 1 are interposed between an object and a screen of an image intensifier.

The positional relationship between the X-ray focal point 2 and the first and second stripes 28 and 30 will be described with reference to FIG. 3. In FIG. 3, for the sake of simplicity, the thickness of the first and second stripes 28 and 30 is assumed to be zero, and the X-ray focal point 2 is assumed to be a point source. Each stripe 28 has a width D and is spaced apart from adjacent stripes 28 at intervals equal to the width D. The stripes 30 are spaced apart from each other at intervals equal to the sizes of the images projected through the intervals between the first stripes 28.

Referring to FIG. 3, the X-ray focal point 2 and the screen 12 have a distance L therebetween, and the screen 12 and the source of the scattered X-rays 8 from the object 6 have a distance L' therebetween. The second stripes 30 and the screen 12 have a distance l1 therebetween, and the first stripes 28 and the screen 12 have a distance l2 therebetween.

The X-ray shielding elements 10 completely shield the X-rays 4 from the X-ray source. The scattered X-rays 8 from the object are incident on the screen 12 of the image intensifier 14 without being spatially modulated by the X-ray shielding elements 10. In order that the scattered X-rays 8 be not spatially modulated, the distances L' and l1 and the width D must satisfy a certain condition.

The function by which the scattered X-rays 8 are not spatially modulated by the X-ray shielding elements 10 will be described with reference to FIGS. 4 and 5.

Figure 4:
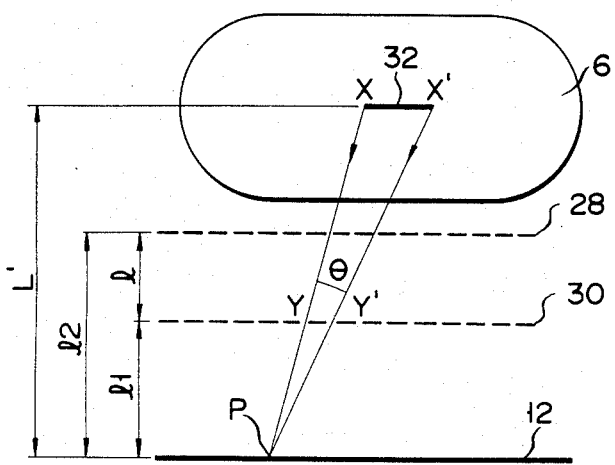
FIGS. 4 and 5 are schematic front diagrams illustrating the positional relationships among the object, the image intensifier screen and the X-ray shielding elements so as to explain why the scattered X-rays are not spatially modulated by the X-ray shielding elements shown in FIG. 1.

Let us assume, as shown in FIG. 4, that the sources of the scattered X-rays 8 are concentrated at the region XX' on a plane 32 which is at the distance L' from the screen. An angle $\theta$ between the points X and X' is approximately XX'/L' radian where XX' is a distance between the points X and X'. When the object 6 is a human body, for example, the distance XX' corresponds to the size of extension of an internal organ or a skeletal member, the size extending in the direction perpendicular to the direction of the X-rays. In this case, the distance XX' can be about 10 mm.

As shown in FIG. 4, in order for the intensity distribution of the scattered X-rays on the screen 12 not to be modulated by the X-ray shielding elements 10, a portion of the second stripes 30 within a distance YY' which corresponds to an angle $\theta$ formed by lines connecting a given point P on the screen 12 and points X and X' on the plane 32, must include one or more of periodic arrangements of the second stripes 30. The member of the periodic arrangements of the second stripes 30 within the distance YY' is approximate to YY'/2D of the first stripes 28. A relation YY':XX'=l1:L' is obtained from a similarity of triangles PYY' and PXX'. The relation yields:

$$l1 \geq 2DL'/XX' \quad (1)$$

Referring to FIG. 4, when the distances L' and l1 and the width D satisfy the relation (1) above, the intensity distribution of the scattered X-rays 8 on the screen 12 will not be modulated by the stripe pattern of the X-ray shielding elements 10. For example, when it is assumed that L'=200 mm and D=1 mm, the distance l1 satisfying the relation (1) is 40 mm or more.

The transmittance of the scattered X-rays through the X-ray shielding elements 10 will be described below.

When it is assumed that the X-ray shielding elements 10 have no thickness in FIG. 3, i.e., l=0, the X-ray shielding elements 10 do not allow passage of the transmitted and scattered X-rays. FIG. 5 illustrates scattered X-rays which are incident on a point Q on the surface of the plate 26 on which the second stripes 30 are formed. As described above, the intensity of X-rays within the distance XX' can be assumed to be constant. If a portion of the first stripes 28 within a distance ZZ' (corresponding to an angle formed by lines connecting the point Q and the points X and X') includes one or more periodic arrangements of the first stripes 28, the intensity distribution of the scattered X-rays on the surface of the plate 28 on which the second stripes 30 are formed is not modulated by the first stripes 28. Note that the member of the periodic arrangements of the first stripes 28 within the distance ZZ' is given by ZZ'/2D. A relation XX':XX'=l:L'−l1 is obtained from a similarity of triangles QZZ' and QXX'. This relation provides:

$$l \geq 2D(L'-l1)/XX' \quad (2)$$

Figure 5:
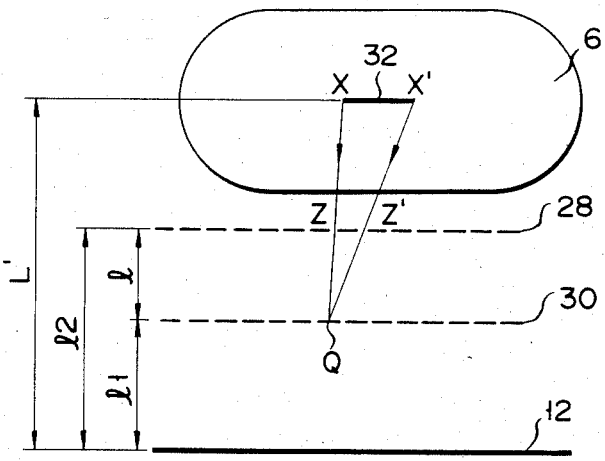

Referring to FIG. 5, the distances L', l and l1 and the width D satisfy the relation (2) above, the X-ray transmittance of the scattered X-rays 8 from the object 6 through the elements 10 becomes maximum. When the X-ray attenuation factor of Al is represented by $\alpha$ mm$^{-1}$ and the sum of the thicknesses of the portions in which the X-ray shielding elements 10 are used as interspacer S is represented by d mm, the maximum transmittance is given by $0.25 \times e^{-\alpha d}$. In this case, it is assumed that the scattered X-rays are perpendicularly incident on the X-ray shielding elements 10. When it is assumed that L'=20 mm, l1=40 mm, D=1 mm, and XX'=10 mm, the distance l satisfying the relation (2) is 32 mm or more.

The first radiographic method using the X-ray radiographic apparatus having the above construction will be described below.

First, before actual radiography, the X-ray shielding elements 10 are inserted between the object 6 and the screen 12 by the driver 22, as shown in FIG. 1. In this case, the positional relationship between the object 6, the X-ray shielding elements 10 and the screen 12 must satisfy the relation (1). X-rays are emitted from the X-ray source and radiography is performed. During radiography, the transmitted primary X-rays are shielded by the X-ray shielding elements 10. Only the scattered X-rays 8 scattered by the object 6 reach the screen 12. Thus, only the scattered X-ray image is recorded in the memory/operation device 18 through the image intensifier 14 and the television camera 16 without being modulated by the stripe pattern of the X-ray shielding elements 10.

Second, after the X-ray shielding elements are removed from the X-ray passing region of the X-ray radiograpic apparatus, a normal transmitted X-ray image which is contaminated with the scattered X-rays is formed on the screen 12. In the same manner as described above, the transmitted X-ray image is recorded as image data in the memory/operation device 18 through the image intensifer 14 and the television camera 16. Meanwhile, the image data of the scattered X-ray image has been intensity-corrected in accordance with the transmittance of the scattered X-rays through the X-ray shielding element 10. The corrected image data of scattered X-rays is subtracted from the image data of the transmitted X-ray image. Then, a correct transmitted primary X-ray image alone is obtained and is displayed on the CRT 20. A scattered X-ray image can be formed after the formation of a transmitted X-ray image. In this case, the same two-dimensional transmitted X-ray image as described above can be obtained.

Even if the object 6 moves slightly during the interval between the first and second radiographies, a resultant change in the scattered X-ray intensity distribution is neglible in most cases, and danger of degrading image quality need not be considered. When continuous radiography is performed in order to obtain a dynamic X-ray image, as long as motion of the object 6 during radiography is relatively small and change in the scattered X-ray intensity distribution is also estimated to be small, the scattered X-ray image taken with the X-ray shielding elements 10 inserted in the apparatus can similarly be subtracted from the transmitted X-ray images, and image corrections for removing the scattered X-ray components can be performed.

When a contrast medium is injected into the object 6 and changes in density of the contrast medium within the object 6 are relatively rapid accompanying rapid changes in the scattered X-ray distribution, if correction is to be performed to eliminate a scattered X-ray component from a transmitted X-ray image at a given moment, time required for completely removing the X-ray shielding elements 10 from the X-ray passing region is excessive. To resolve this problem, a second method according to the present invention will be described below.

First, the plate 26 on the rear surface of which the second stripes 30 are formed is slid relative to the front surface of the plate 24 on which the first stripes 28 are formed for a distance corresponding to one stripe pitch along a direction perpendicular to the longitudinal direction of the stripes 28. Then, the first radiography is performed, and a first transmitted X-ray image is recorded in the memory/operation device 18 through the image intensifier 14 and the television camera 16. Second, both the plate 24 (on the front surface of which the first stripes 28 are formed) and the plate 26 (on which the second stripes 30 are formed) are slid for a distance corresponding to each stripe pitch in the same direction perpendicular to the longitudinal direction of each stripe. Then, the second radiography is performed and a second transmitted X-ray image is similarly recorded in the memory/operation device 18. The memory/operation device 18 adds the first and second transmitted X-ray images and a resultant normal transmitted X-ray image is re-stored. In this case, it must be considered that the quantity of the scattered X-ray components is twice that of the scattered X-ray components of a transmitted X-ray image formed by a single radiographic operation. When a normal transmitted X-ray image is formed by two radiographic operations, the stripe patterns and the scanning pattern of the television camera 16 may interfere with each other. In order to prevent such interference, the scanning direction of the television camera 16 is preferably set to be perpendicular to the longitudinal direction of the stripes.

In the above description, the X-ray focal point 2 is assumed to be sufficiently small. However, in practice, the X-ray focal point 2 has a finite length. For this reason, the projection pattern on the second stripes 30 is blurred due to X-rays transmitted through intervals between the first stripes 28. When a magnification of the X-ray region on the second stripes 30 corresponding to that of X-rays transmitted through intervals between the first stripes 28 is represented by M, it can be given as $M=(L-l1)/(L-l2)$ from the geometric relationship illustrated in FIG. 3. The second stripes 30 have a width MD which is enlarged with respect to D of the first stripes 28. When a size of the X-ray focal point 2 in a direction parallel to the plane of the second stripes 30 is represented by f, the width of the second stripes 30 has an error of f(M−1) from the value MD. In other words, the transmitted primary X-rays cannot be completely shielded by the X-ray shielding elements 10. In view of this, the width of the second stripes 30 must be increased by at least f(M−1) in a predetermined direction, or the width of the first stripes 28 must be increased by at least f(M−1)/M. For example, if L=1,000 mm, l1=40 mm, l=32 mm, and f=1 mm, and f=1 mm, f(M−1)≃0.034 mm. When the width of the second stripes 30 is increased by this value, the transmittance of the scattered X-rays through the X-ray shielding elements 10 is not substantially influenced.

The above description is exemplified with respect to the case wherein the distance l1 satisfies the relation (1). According to the method of the present invention, even if the distance l1 does not satisfy the relation (1), i.e., even if the distance l1 is very small, a scattered X-ray image can be obtained by adopting the principle of a Bucky grid in the X-ray radiographic apparatus of the present invention.

During formation of a scattered X-ray image, both the X-ray shielding elements 10 are shifted or vibrated for a distance corresponding to one stripe pitch or more along the direction perpendicular to the longitudinal direction of the stripes 28 and 30. Then, the scattered X-rays are not modulated by the stripe pattern. However, when the shifting distance is too large, the primary X-rays 4 cannot be shielded by the X-ray shielding elements 10. In order to avoid this problem, the moving distance of the X-ray shielding elements 10 during radiography must be limited. Therefore, the width of the first stripe 28 or second stripe 30 must be greater than those shown in FIG. 3.

A second embodiment of an X-ray radiographic apparatus according to the present invention will be described with reference to FIG. 6. The same reference numerals as in FIGS. 1 to 3 denote the same parts in FIG. 6.

The difference between the X-ray radiographic apparatuses shown in FIG. 6 and in FIGS. 1 to 3 will be described below. In this embodiment, the X-ray radiographic apparatus has first and second X-ray shielding elements 34 and 36. The first X-ray shielding element 34 is interposed between an X-ray focal point 2 and an object 6. The second X-ray shielding element 36 is interposed between the object 6 and a screen 12 of an image intensifier 14. As shown in FIG. 6, the first and second X-ray shielding elements 34 and 36 have plates 38 and 40 consisting of a substance of a small X-ray attenuation factor. A number of stripes 42 and 44, respectively, are regularly mounted on these plates 38 and 40. The stripes 42 and 44 consist of a substance of a large X-ray attenuation factor. Drivers 46 and 48 are mounted above the first and second X-ray shielding elements 34 and 36.

The positional relationship between the stripes 42 and 44 and the X-ray focal point 2 will be described below. In this case, as described above with reference to FIG. 3, it is assumed that the thickness of the stripes 42 and 44 is zero and the X-ray focal point 2 is a point source. The arrangement of the stripes 42 and 44 is similar to that of the stripes 28 and 30 in FIG. 3 except that the object 6 is inserted between the stripes 42 and 44 in FIG. 6. Therefore, in FIG. 7, the primary X-rays are completely shielded by the stripes 42 and 44 and do not reach the screen 12 of the image intensifier 14. As long as the distances L' and l1 and the width D satisfy the relation (1) described with reference to the first embodiment, the scattered X-rays from the object 6 reach the screen 12 of the image intensifier 14 without being modulated by the stripes 42 and 44.

A radiographic method using the X-ray radiographic apparatus according to the second embodiment will be described below. This method is the same as that described with reference to the first embodiment except in the following respects. In forming a scattered X-ray image, the first X-ray shielding element 34 is inserted between the X-ray focal point 2 and the object 6, and the second X-ray shielding element 36 is inserted between the object 6 and the screen 12. The X-ray shielding elements 34 and 36 satisfy the relation (1) above.

The X-ray radiographic method to be used in the X-ray radiographic apparatus of the second embodiment has the following advantages.

First, the distance between the object 6 and the image intensifier 14 can be significantly reduced. In the X-ray radiographic apparatus shown in FIG. 1, in order to increase the transmittance of the scattered X-rays 8 through the X-ray shielding element 26, the distance L' between the object 6 and the screen 12 must be larger than that in the X-ray radiographic apparatus shown in FIG. 6. This is because the distance l between the stripes 42 and 44 of the apparatus shown in FIG. 6 is larger than that of the apparatus shown in FIG. 1. Second, since approximately half of the irradiated X-rays from the source of X-ray is shielded by the first X-ray shielding element 34, when a scattered X-ray image is formed, the X-ray dose of the object 6 can be reduced to approximately half that of the apparatus of the first embodiment.

In both the X-ray radiographic apparatuses shown in FIGS. 1 and 6, if the amount of scattered X-rays emerging from the X-ray shielding elements 10, 34 and 36 is not negligible when a normal transmitted X-ray image formed by X-rays transmitted through the object 6 and the elements 10, 34 and 36 is formed. Removal of the X-ray shielding elements 10, 34 and 36 from the X-ray passing region results in the following problem.

When an image is formed after removing the elements 10, 34 and 36 from the X-ray passing region, scattered X-rays involved in forming a normal transmitted X-ray image are entirely generated from the object 6. In contrast to this, when the elements 10, 34 and 36 are used during radiography, scattered X-rays involved in forming a transmitted X-ray image are from the object 6 and also the elements 10, 34 and 36. Therefore, if the two images, that is, the normal transmitted X-ray image and the scattered X-ray image are combined by subtraction, a correct transmitted X-ray image cannot be obtained. In order to resolve this problem, there are three modified embodiments using the above described apparatuses.

First, in the apparatuses shown in FIG. 1 or 6, when the amount of scattered X-rays coming from the X-ray shielding elements 10, 34 and 36 is not negligible, two images are recorded as described with reference to the first embodiment. More specifically, the first image is taken after the first stripes 28 or 42 are slid by one pitch relative to the second stripes 30 or 44 in the direction perpendicular to the longitudinal direction of the stripes in contrast to the geometry shown in FIG. 1 or 6. The second image is taken after the second stripes 30 or 44 are slid by one pitch relative to the first stripes 28 or 42 in the direction perpendicular to the longitudinal direction of the stripes in contrast to the geometry shown in FIG. 1 or 6. The image data are respectively stored in the memory/operation device 18 and are combined. A resultant reproduced image can be used as the normal transmitted X-ray image.

Second, in the apparatuses shown in FIG. 1 or 6, the normal transmitted X-ray image is formed by vibrating each of the first and second X-ray shielding elements 10, 34 and 36. In this forming, it is possible that a part of the X-rays transmitted through the object 6 is transmitted through the first X-ray shielding element 10, 34, and transmitted through the second X-ray shielding element 10, 36 such that the condition of each of the first and second X-ray shielding elements 10, 34 and 36 is adjusted so that an image formed by the X-ray transmitted through the first and second X-ray shielding elements 10, 34 and 36 is not modulated by the stripe pattern of the first and second X-ray shielding elements 10, 34 and 36. A resultant reproduced image can be used as the normal transmitted X-ray image.

Third, when X-ray shielding elements shown in FIG. 9, detailed hereinafter, are used, the scattered X-rays from the elements need not be considered. This is because the X-ray shielding elements 82 shown in FIG. 9 do not have an interspacer.

Next, a third embodiment of the present invention will be described with reference to FIG. 7. The same reference numerals as in FIGS. 1 to 3 denote the same parts in FIG. 7.

The difference between the X-ray radiographic apparatuses shown in FIGS. 1 and 7 will first be described. First, in this embodiment, two X-ray focal points 50 and 52 are present. The X-ray focal points 50 and 52 are at a given distance L from a screen 12 of an image intensifier 14. As in the case of the X-ray shielding elements 10 shown in FIG. 1, X-ray shielding elements 54 and 56 shown in FIG. 7 are inserted between an object 6 and the screen 12 and have plates 58 and 60, respectively. A number of first and second stripes 62 and 64 are respectively formed on the front surface of the plate 58 facing the object 6 and on the rear surface of the plate 60 facing the screen 12. As described in the case of the first embodiment, it is assumed that the X-ray sources are point sources and the thickness of the stripes 62 and 64 is sufficiently small. As shown in the case of FIG. 3, the first stripes 62 have a width D and are spaced apart by intervals D parallel to each other. The second stripes 64 are arranged so that its intervals overlap the projection images formed by beams from the focal point 50 through the intervals between the first stripes 62. The second stripes 64 are also arranged to overlap the projection images formed through intervals between the first stripes 62 obtained with beams from the focal point 52.

A distance $\delta$ between the two focal points 50 and 52 when the X-ray shielding elements 54 and 56 have the above-described structure will be described.

The distance between the two focal points 50 and 52 must satisfy the positional relationship between the first and second stripes 62 and 64 and the focal points 50 and 52. Although a number of positions satisfy this requirement for the focal point 52, a position among such positions closest to the focal point 50 is preferable. In this case, from the similarity of two resulting triangles, the distance $\delta$ between the focal points 50 and 52 is given by:

$$\delta = D(L - l1)/l \qquad (3)$$

when it is assumed as practical values that D=1 mm, L=1,000 mm, l1=40 mm, and l=32 mm, $\delta$=30 mm is obtained from the relation (3).

An X-ray radiographic method for obtaining a transmitted X-ray image from which a scattered X-ray image component is removed by the X-ray radiographic apparatus shown in FIG. 7 will be described below.

As in the case of the first embodiment, when the object 6 is radiographed with X-rays from the focal point 52, only a scattered X-ray image is formed by the X-ray shielding elements 54 and 56. When the object 6 is radiographed with X-rays from the focal point 50, a normal transmitted X-ray image is modulated by the X-ray shielding elements 54 and 56. In order that an image obtained with X-rays from the focal point 50 be not modulated by the stripes 62 and 64, the principle of a Bucky grid can be adopted. During radiography of the object 6 by X-rays from the focal point 50, both the X-ray shielding elements 54 and 56 are moved or vibrated for a distance corresponding to one pitch or more of the stripes along a direction perpendicular to the longitudinal direction of the stripes. Then, the image is not modulated by the stripes 62 and 64. Also, during radiography of the object 6 by X-rays from the focal point 52, both the X-ray shielding elements 54 and 56 are preferably moved or vibrated for a distance corresponding to one pitch or more of stripes in a direction perpendicular to the longitudinal direction of the stripes. This is the same as described with reference to the second method using the X-ray radiographic apparatus according to the first embodiment of the present invention.

In this embodiment, a slight change in the incident angle of X-rays does not result in a change in intensity distribution of the scattered X-rays. This is because the intensity of the scattered X-rays from a point of the object 6 shows a fairly weak dependence on the scattering angle. The difference $\theta$ in incident angle of the primary X-rays 4 emitted from the focal points 50 and 52 to a given point in the object 6 is approximately given by $\delta/(L-L')$ radian. Where L' is a distance between the given point in the object 6 and the screen 12. When it is assumed, as practical values, that $\delta$=30 mm, L=1,000 mm, and L'=200 mm, the difference $\theta$ in incident angle becomes 0.04 radian, i.e., about 2.1 degrees. This value is small. Therefore, the scattered X-rays in a transmitted X-ray image originated from the focal point 50 become about the same as those in a scattered X-ray image originated from the focal point 52.

When the memory/operation device 18 performs a subtraction operation of the obtained scattered and transmitted X-ray images, a correct transmitted X-ray image is displayed on the CRT 20.

Even if the recorded image is modulated by the stripe pattern, as long as it does not hinder normal diagnosis (e.g. inspection), or the width D of the stripes, as an output image of the image intensifier 14, is such a small value that it is impossible to satisfy the resolution limit width of the television camera 16, the X-ray shielding elements 54 and 56 need not be moved or vibrated and can be fixed in position.

When the above method is utilized, a scattered X-ray image component at a given instant can be correctly removed to a certain extent even if a contrast medium is injected into the object 6, the contrast medium in the object 6 is flowing, changes in density distribution of the contrast medium are very rapid accompanying rapid changes in the scattered X-ray distribution.

In the X-ray radiographic apparatus shown in FIG. 7, all the radiographic operations are performed while the X-ray shielding elements 54 and 56 are inserted between the object 6 and the screen 12 of the image intensifier 14. Therefore, the scattered X-rays emerging from the X-ray shielding elements 54 and 56 are completely removed by the subtraction operation. For this reason, the amount of scattering by the X-ray shielding elements can be large.

Figure 8:
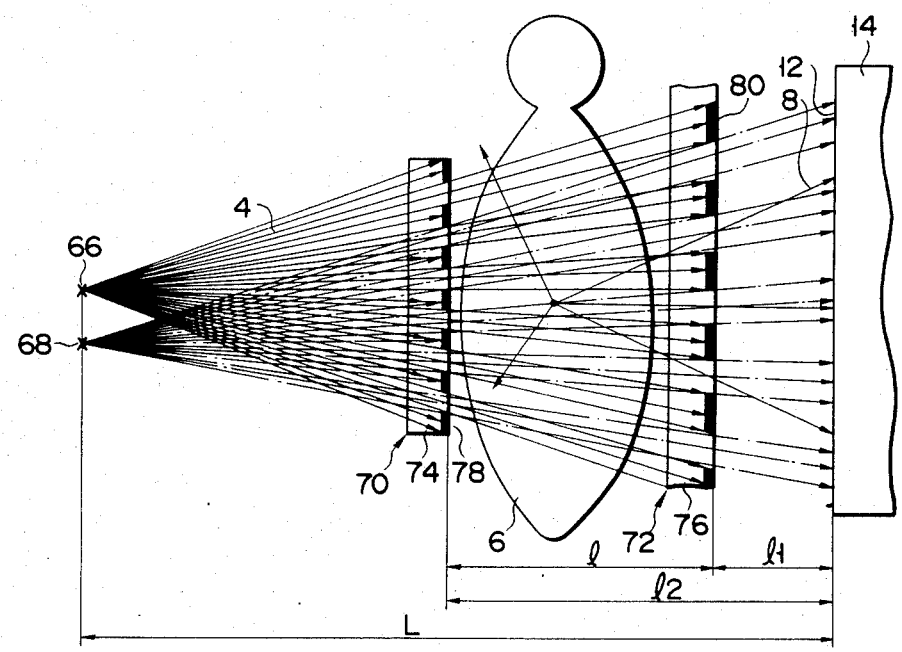

FIG. 8 shows an X-ray radiographic apparatus according to a fourth embodiment of the present invention which uses two focal points similar to those shown in FIG. 7. In this X-ray radiographic apparatus, as in the case of the apparatus shown in FIG. 6, first and second X-ray shielding elements 70 and 72 are arranged before and after an object. The first and second X-ray shielding elements 70 and 72 comprise plates 74 and 76 with a number of stripes 78 and 80. In the radiographic method to be adopted in this apparatus, as in the case of FIG. 8, a scattered X-ray image is formed on a screen 12 by X-rays from an X-ray focal point 66 and a normal transmitted X-ray image is formed on the screen 12 by X-rays from an X-ray focal point 68.

In the third and fourth embodiments, when X-rays from the focal points 50 and 52, or, 66 and 68 are not equally incident on the object 6, an X-ray dose meter or an X-ray dose rate meter is arranged at a position within the X-ray passing region between the focal points 50 and 52 and the object 6 or at the vicinity of the position. The X-ray dose meter or X-ray dose rate meter measures the X-ray dose or X-ray dose rate. The radiographic image data is corrected in accordance with the measured X-ray dose or X-ray dose rate, and a correct transmitted X-ray is displayed on the CRT 20.

In X-ray radiographic apparatuses of the third and fourth embodiments, two X-ray tubes can be used as the two X-ray focal points. Alternatively, a single X-ray source can be used and can be shifted between two positions. A bifocal X-ray tube used in stereoscopic X-ray radiography can also be used. When the bifocal X-ray tube is used as the X-ray point sources, the problem in which the distance δ between the focal points 50 and 52, or, 66 and 68 cannot be reduced below a predetermined value can be eliminated.

Modifications of the X-ray shielding elements shown in FIGS. 1, 7 and 8 will be described with reference to FIGS. 9 to 12.

Figure 9:
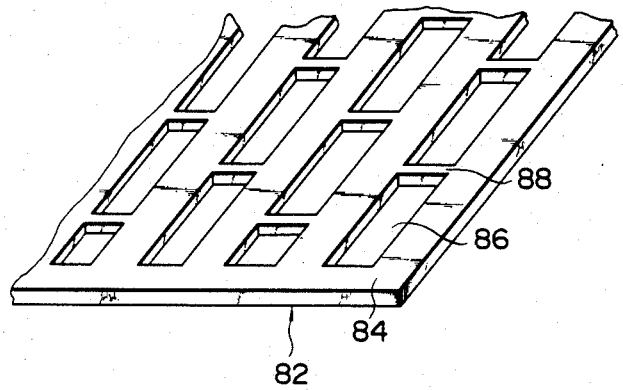
FIGS. 9 to 11 are perspective view respectively illustrating modifications of the X-ray shielding elements of the X-ray radiographic apparatus according to the present invention.

An X-ray shielding element 82 shown in FIG. 9 comprises a plate 84 which does not transmit X-rays and holes 86 are regularly formed in the plate 84. The holes 86 correspond to the X-ray passing portions between adjacent stripes of the X-ray shielding elements. Bridges 88 are formed between the longitudinally adjacent holes 86 so as to reinforce the plate 84.

When two types of X-ray shielding elements 82 having different patterns of holes 86 are arranged, they can completely shield the primary X-rays 4 from the X-ray source without using an interspacer. Therefore, the scattered X-rays caused by the X-ray shielding element 82 are largely reduced as compared with the element having the interspacer.

Figure 10:
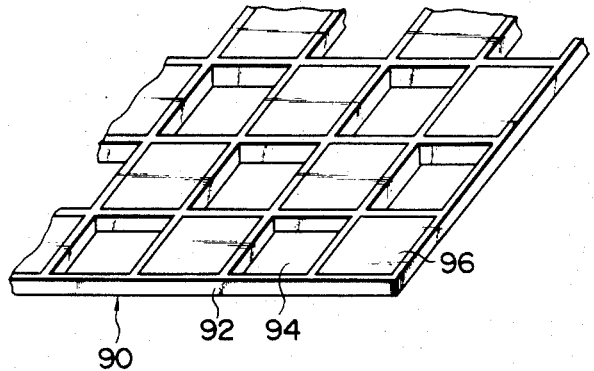

FIG. 10 shows an X-ray shielding element 90 of a different structure. The element 90 has a lattice-like wall member 92 which has a number of regularly distributed holes 94. X-ray shielding members 96 are arranged in these holes 92 in a staggered manner. When two types of X-ray shielding elements 90 having different patterns of members 96 are arranged, they can completely shield transmitted X-rays as in the case of the elements of the former embodiments and modifications.

Figure 11:
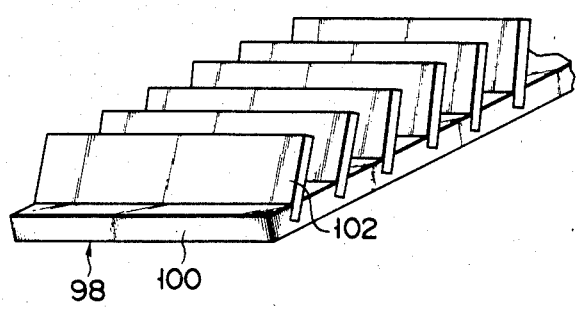
Figure 12:
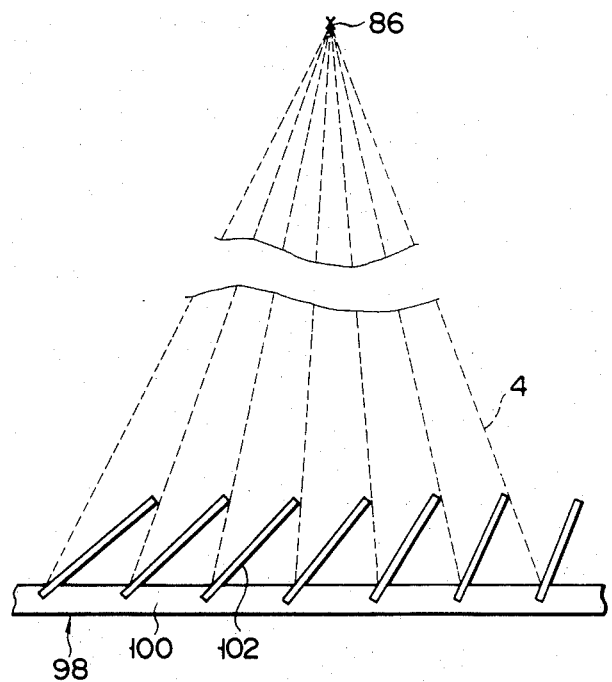
FIG. 12 is a side view illustrating X-ray shielding elements so as to explain the structure of the element shown in FIG. 11.

FIGS. 11 and 12 show still another X-ray shielding element 98. The X-ray shielding element 98 has a plate 100 of a material which transmits X-rays. A lower end of each X-ray shielding member 102 is inserted in the plate 100 at a predetermined angle. As illustrated in FIG. 12, the angle between each member 102 and the plate 100 is set such that the primary X-rays 4 from an X-ray focal point 104 can be completely shielded by the members 102.

The single X-ray shielding element 98 of the above structure can completely shield primary X-rays.

In the X-ray radiographic apparatuses of the first to fourth embodiments, the image intensifier 14 is used as an image converter, and the television camera 16 is used as a converted image reader. However, according to the present invention, other types of image converters and converted image readers can be used.

The above embodiments are described with reference to the case wherein the present invention is applied to an X-ray radiographic apparatus. However, according to the present invention, radiation beams other than X-rays, for example, α-rays, β-rays, γ-rays, neutron beams, ultraviolet rays, visible light rays, infrared rays, or far-infrared rays can be used.

What is claimed is:

1. A radiographic method for irradiating an object with a radiation beam and for obtaining a two-dimensional image of the object based upon a beam transmitted through the object, comprising:

arranging first and second shielding means to be movable between first and second states when the object is irradiated with the radiation beam, the first and second shielding means passing to an image converter transmitted primary radiation beams not scattered by the object and scattered radiation beams scattered by the object in the first state, and in the second state the first and second shielding means shielding the transmitted primary radiation beams and passing to the image converter scattered radiation beams;

forming, in a form of electrical signals, a first radiation image of the object when the object is irradiated with the radiation beam while the first and second shielding means are in the first state, and forming, in the form of electrical signals, a second radiation image when the object is irradiated with the radiation beam while the first and second shielding means are in the second state; and processing, reproducing and displaying a two-dimensional image of the object by electrically processing the first and second radiation images obtained in the image forming step, the two-dimensional image being substantially free from the influence of spatial modulation caused by the first and second shielding means and substantially free from the influence of the scattered radiation beams.

2. A method according to claim 1, wherein the image forming step includes: a screen reception step for receiving the transmitted primary radiation beams and the scattered radiation beams with an image converter, a conversion step for converting the received image into a converted image, an imaging step for imaging the converted image, and an electrical conversion step for electrically converting the image into image data; and wherein the processing step includes: a processing step for storing the image data and processing the image data of the first and second radiation images into image data of the radiation images, and a displaying step for reproducing and displaying the image data of the radiation images.

3. A method according to claim 1, wherein the arranging step includes the steps of (a) arranging, between the object and the image converter, the first shielding means for passing the transmitted primary radiation beams and the scattered radiation beams, and the second shielding means for shielding the transmitted primary radiation beams transmitted through the first shielding means and for passing the scattered radiation beams transmitted through the first shielding means, and (b) arranging a driver for switching said first and second shielding means to one of the first and second states.

4. A method according to claim 3, wherein the (b) arranging step includes the steps of: (b1) arranging, with said driver, the first and second shielding means in the second state, and (b2) moving, with said driver, the first and second shielding means relative to each other in a direction substantially perpendicular to a propagating direction of the transmitted primary radiation beams to switch the first and second shielding means to the first state.

5. A method according to claim 3, wherein the (b) arranging step includes the steps of: (b1) arranging, with said driver, the first and second shielding means in the second state, and (b2) continuously moving, with said driver, the first and second shielding means relative to each other with a velocity-component of the relative movement being substantially perpendicular to a propagating direction of the transmitted radiation beams to switch the first and second shielding means to the first state.

6. A method according to claim 1, wherein the arranging step includes the steps of (a) arranging the first shielding means for passing some of incident radiation beams, and the second shielding means for shielding the transmitted radiation beams transmitted through the first shielding means and the object and for passing the scattered radiation beams, and (b) arranging a driver for switching said first and second shielding means to one of the first and second states.

7. A method according to claim 6, wherein the (b) arranging step includes the steps of: (b1) arranging, with said driver, the first and second shielding means in the second state, and (b2) moving, with said driver, the first and second shielding means relative to each other in a direction perpendicular to a propagating direction of the transmitted primary radiation beams to switch the first and second shielding means to the first state.

8. A method according to claim 6, wherein the (b) arranging step includes the steps of: (b1) arranging, with said driver, the first and second shielding means in the second state, and (b2) continuously moving the first and second shielding means relative to each other with a velocity-component of the relative movement being substantially perpendicular to a propagating direction of the transmitted radiation beams to switch the first and second shielding means to the first state.

9. A method according to claim 1, wherein the arranging step includes the steps of: (a) arranging, with said driver, the first and second shielding means in a passing region of the transmitted primary radiation beams to cause the first and second shielding means to be in the second state, and (b) removing, with said driver, at least one of the first and second shielding means from the passing region of the transmitted primary radiation beams to switch the first and second shielding means to the first state.

10. A method according to claim 1, wherein the arranging step includes the step of continuously moving the first and second shielding means relative to each other such that a velocity-component of the relative movement is substantially perpendicular to a propagating direction of the transmitted radiation beams in at least one of the first and second states.

11. A radiographic method for irradiating an object with a conical radiation beam and for obtaining a two-dimensional transmitted image of the object based upon a beam transmitted through the object, comprising:
arranging radiation shielding means;
irradiating said object with radiation beams from different positions;
allowing the shielding means to pass to an image converter some of transmitted primary radiation beams not scattered by but transmitted through the object and some of scattered radiation beams scattered by the object so as to obtain, in a form of electrical signals, a first radiation image of the object when the object is irradiated from at least one of the positions, and allowing the radiation shielding means to shield the transmitted primary radiation beams and to pass to the image converter some of the scattered radiation beams so as to obtain, in the form of electrical signals, a second radiation image of the object when the object is irradiated from at least one of the positions; and
obtaining the two-dimensional transmitted image of the object by electrically processing the first and second radiation images obtained in the image forming step, the two-dimensional transmitted image being substantially free from the influence of spatial modulation caused by the radiation shielding means, and substantially free from the influence of the scattered radiation beams.

12. A method according to claim 11, wherein the image forming step includes the steps of: (a) receiving the transmitted primary radiation beams and the scattered radiation beams at the image converter, (b) converting the received image into a converted image, (c) imaging the converted image, and (d) electrically converting the image into image data; and wherein the processing step includes the steps of: (a) storing the image data and processing the image data of the first and second radiation images into image data of the radiation images, and (b) reproducing and displaying the image data of the radiation images.

13. A method according to claim 11, wherein the arranging step includes the step of arranging first and second radiation shielding elements to cause the first radiation shielding element to pass some of the transmitted primary radiation beams and some of the scattered radiation beams when the object is irradiated from the different positions, and to cause the second radiation shielding element to pass some of the transmitted radiation beams transmitted through the first radiation shielding element when the object is irradiated from one of said different positions, and to cause the second radiation shielding element to shield the transmitted primary radiation beams transmitted through the first radiation shielding element and to pass some of the scattered radiation beams transmitted through the first radiation shielding element when the object is irradiated from a second one of said different positions.

14. A method according to claim 11, wherein the arranging step includes the step of arranging first and second radiation shielding elements to cause the first radiation shielding element to pass some incident radiation beams when the object is irradiated from the different positions, and to cause the second radiation shielding element to pass some of the transmitted primary radiation beams and some of the scattered radiation beams transmitted through the first radiation shielding element and the object when the object is irradiated from one of said different positions, and to cause the second radiation shielding element to shield the transmitted primary radiation beams transmitted through the first radiation shielding element and the object and to pass some of the scattered radiation beams transmitted through the first radiation shielding element when the object is irradiated from a second one of said different positions.

15. A method according to claim 11, wherein the arranging step includes the step of continuously moving at least a portion of said radiation shielding element so that a velocity-component of the continuous movement is substantially perpendicular to a propagating direction of the transmitted primary radiation beams during the irradiating step.

16. A radiographic apparatus for irradiating an object with a conical radiation beam and for obtaining a two-dimensional transmitted image of the object based upon a beam transmitted through the object, comprising:
irradiating means for irradiating the object with primary radiation beams of conical shape from a radiation source at least two times while the object is at a position with respect to the radiation source;
first and second shielding means arranged in a primary radiation beam passing region and being movable between first and second states, the first and second shielding means passing both some of transmitted primary radiation beams transmitted through the object and some of scattered radiation beams scattered by the object when the first and second shielding means are in the first state, the first and second shielding means shielding the transmitted primary radiation beams and passing some of the scattered radiation beams when the first and second shielding means are in the second state;

an image converter arranged on an opposite side of said first and second shielding means from the radiation source and having a screen opposing the object, the image converter receiving a first radiation image on the screen and converting the first radiation image into a first converted image when the first and second shielding means are in the first state, and the image converter receiving a second radiation image on the screen and converting the second radiation image into a second converted image when the first and second shielding means are in the second state;

imaging means, arranged to oppose the first and second converted images of the image converter, for converting the first and second converted images of the first and second radiation images into electrical signals to obtain image data; and reproduction/display means, electrically coupled to the imaging device, for storing the image data of the first and second radiation images and electrically processing the image data of the first radiation image, and for reproducing and displaying the two-dimensional transmitted image of the object which is substantially uninfluenced by the scattered radiation beams.

17. An apparatus according to claim 16, wherein the first and second shielding means are interposed between the object and the screen of the image converter, and wherein said first shielding means passes some of the transmitted primary radiation beams and some of the scattered radiation beams, and wherein said second shielding means is arranging at a predetermined distance from the first shielding means in a direction toward the screen of the image converter, said second shielding means shielding the transmitted primary radiation beams and passing some of the scattered radiation beams, and further including driver means for switching the first and second shielding means between said first and second states.

18. An apparatus according to claim 17, wherein the first and second shielding means have surfaces opposing each other, each said surface including (a) a substance having a small radiation attenuation factor, and (b) a plurality of stripes, each of said stripes including a substance having a large radiation attenuation factor, the stripes of the first and second shielding means being substantially parallel to each other.

19. An apparatus according to claim 17, wherein said driver means moves said first and second shielding means to and from a primary radiation beam passing region between the radiation source and the image converter, to switch the first and second shielding means between the first and second states.

20. An apparatus according to claim 17, wherein during reception of at least one of the first and second radiation images, said driver means continuously moves at least one of the first and second shielding means with a velocity-component substantially perpendicular to a propagating direction of the transmitted primary radiation beams.

21. An apparatus according to claim 17, wherein said driver means shifts the first and second shielding means relative to each other with a displacement-component substantially perpendicular to a propagating direction of the transmitted radiation beams, to switch the first and second shielding means between the first and second states.

22. An apparatus according to claim 16, wherein said first shielding means is interposed between the radiation source and the object and transmits some of the radiation beams from the radiation source, and wherein said second shielding means is interposed between the object and the screen at a predetermined distance from the first shielding means to shield the transmitted primary radiation beams transmitted through the first shielding means and the object, and to transmit some of the scattered radiation beams; and further including driver means for switching the first and second shielding means between the first and second states.

23. An apparatus according to claim 22, wherein the first and second shielding means have surfaces opposing each other, each surface comprising (a) a substance having a small radiation attenuation factor, and (b) a plurality of stripes, each of said stripes including a substance having a large radiation attenuation factor, the stripes of the first and second shielding means being substantially parallel to each other.

24. An apparatus according to claim 22, wherein said driver means moves said first and second shielding means to and from a primary radiation beam passing region between the radiation source and the image converter, to switch the first and second shielding means between the first and second states.

25. An apparatus according to claim 22, wherein, during reception of at least one of the first and second radiation images, said driver means continuously moves at least one of the first and second shielding means with a velocity-component substantially perpendicular to a propagating direction of the transmitted primary radiation beams.

26. An apparatus according to claim 22, wherein said driver means shifts the first and second shielding means relative to each other with a displacement-component substantially perpendicular to a propagating direction of the transmitted radiation beams, to switch the radiation shielding elements between the first and second states.

27. A radiographic apparatus for irradiating an object with a conical radiation beam and for obtaining a two-dimensional transmitted image of the object based upon a beam transmitted through the object, comprising:

irradiating means for irradiating the object from first and second positions;

radiation shielding means, arranged in a primary radiation beam passing region, for passing some of transmitted primary radiation beams and some of scattered radiation beams when the irradiating means irradiates from the first position, and for shielding the transmitted primary radiation beams transmitted through the object while passing some of the scattered radiation beams scattered by the object when the irradiating means irradiates from the second position;

an image converter arranged on an opposite side of shielding means from the irradiating means and having a screen facing the object, the image converter receiving a first radiation image on the screen and converting the first radiation image into a first converted image when the irradiating means irradiates the object from the first position, and the image converter receiving a second radiation image on the screen and converting the second radiation image into a second converted image when the irradiating means irradiates the object from the the second position;

imaging means, arranged to oppose the first and second converted images of the image converter, for converting the first and second converted images into electrical signals, thereby obtaining image data; and reproduction/display means, electrically coupled to the imaging means, for storing the image data of the first and second radiation images, and for electrically processing the image data of the first radiation image, to produce and display a two-dimensional transmitted image of the object which is substantially free from the influence of the scattered radiation beams.

28. An apparatus according to claim 27, wherein the radiation shielding means includes first and second radiation shielding elements arranged between the object and the screen of the image converter, and further including a driver for switching the first and second radiation shielding elements between first and second states, the first radiation shielding element passing some of the transmitted primary radiation beams and some of scattered radiation beams when the object is irradiated from the first and second positions, the second radiation shielding element passing the transmitted primary radiation beams and some of the scattered radiation beams transmitted through the first radiation shielding element when the object is irradiated from the first position, and the second radiation shielding element shielding the transmitted primary radiation beams transmitted through the first radiation shielding element while passing some of the scattered radiation beams transmitted through the first radiation shielding element when the object is radiated from the second position.

29. An apparatus according to claim 28, wherein said first and second radiation shielding elements have surfaces opposing each other, each surface comprising (a) a substance having a small radiation attenuation factor, and (b) a plurality of stripes, each of said stripes including a substance having a large radiation attenuation factor, the stripes of the first and second radiation shielding elements being substantially parallel to each other.

30. An apparatus according to claim 29, wherein said driver means continuously moves at least one of the first and second radiation shielding elements with a velocity-component of the continuous movement being substantially perpendicular to a propagating direction of the transmitted primary radiation beams when the object is irradiated from at least one of first and second positions.

31. An apparatus according to claim 27, wherein the radiation shielding means includes a first radiation shielding element which is interposed between the irradiating means and the object, a second radiation shielding element which is interposed between the object and the screen of the image converter, and a driver for switching the first and second radiation shielding elements between first and second states, the first radiation shielding element passing some incident radiation beams when the object is irradiated from the first and second positions, the second radiation shielding element passing some of the transmitted primary radiation beams and some of the scattered radiation beams transmitted through the first radiation shielding element and the object when the object is irradiated from the first position, and the second radiation shielding element shielding the transmitted primary radiation beams transmitted through said first radiation shielding element and the object while passing some of the scattered radiation beams transmitted through the first radiation shielding element when the object is irradiated from the second position.

32. An apparatus according to claim 31, wherein said first and second radiation shielding elements have surfaces opposing each other, each surface including (a) a substance having a small radiation attenuation factor, and (b) a plurality of stripes, each stripe including a substance having a large radiation attenuation factor, the stripes of the first and second radiation shielding elements being substantially parallel to each other.

33. An apparatus according to claim 32, wherein said driver continuously moves at least one of the first and second radiation shielding elements with a velocity-component of the continuous movement being substantially perpendicular to a propagating direction of the transmitted primary radiation beams when the object is irradiated from at least one of the first and second positions.

34. An apparatus according to claim 27, wherein said irradiating means comprises a dual-focus radiation tube having two focal points within a single vacuum tube.

* * * * *